United States Patent [19]

Hutchison

[11] Patent Number: 5,504,202
[45] Date of Patent: Apr. 2, 1996

[54] SUCROSE POLYESTER USEFUL AS FAT SUBTITUTE AND PREPARATION PROCESS

[75] Inventor: Robert B. Hutchison, Cincinnati, Ohio

[73] Assignee: Henkel Corporation, Plymouth Meeting, Pa.

[21] Appl. No.: 223,203

[22] Filed: Apr. 5, 1994

[51] Int. Cl.$^6$ .................. C08B 37/00; C07H 13/06; C07H 13/00
[52] U.S. Cl. .................. 536/124; 536/115; 536/116; 536/119; 536/120; 554/168; 426/601; 426/611; 426/804
[58] Field of Search .................. 536/115, 116, 536/119, 120, 124; 426/601, 611, 804; 554/168

[56] References Cited

U.S. PATENT DOCUMENTS

| | | | |
|---|---|---|---|
| 3,600,186 | 8/1971 | Mattson | 536/124 |
| 3,963,699 | 6/1976 | Rizzi et al. | 536/124 |
| 4,005,195 | 1/1977 | Jandacek | 536/124 |
| 4,034,083 | 7/1977 | Mattson | 536/124 |
| 4,611,055 | 9/1986 | Yamamoto et al. | 536/119 |
| 4,880,657 | 11/1989 | Guffey et al. | 426/611 |
| 4,931,552 | 6/1990 | Gibson et al. | 536/119 |
| 4,954,621 | 9/1990 | Masaoka et al. | 536/119 |
| 5,071,669 | 12/1991 | Seiden | 426/611 |
| 5,077,073 | 12/1991 | Ennis et al. | 536/116 |
| 5,079,355 | 1/1992 | Grechke et al. | 536/119 |
| 5,085,884 | 2/1992 | Young et al. | 426/611 |
| 5,194,281 | 5/1992 | Johnston et al. | 536/119 |
| 5,236,733 | 8/1993 | Zimmerman et al. | 426/611 |
| 5,314,707 | 5/1994 | Kester et al. | 426/611 |
| 5,366,753 | 11/1994 | Meyer et al. | 426/611 |

*Primary Examiner*—Ronald W. Griffin
*Attorney, Agent, or Firm*—Ernest G. Szoke; Wayne C. Jaeschke; Real J. Grandmaison

[57] ABSTRACT

A process for preparing a sucrose fatty acid polyester comprising mixing a sucrose ether having an average degree of etherification of from about 4 to about 8 with a basic catalyst and an excess of a fatty acid lower alkyl ester, heating the resultant mixture to a temperature of from about 120° C. to about 180° C. at a pressure of up to about 10 mm of mercury while removing the alcohol formed during the formation of the sucrose fatty acid polyester, and then separating the sucrose fatty acid polyester from the reaction mixture. The sucrose fatty acid polyester is a synthetic low calorie fat substitute and is useful in preparing edible non-digestible food products.

9 Claims, No Drawings

SUCROSE POLYESTER USEFUL AS FAT SUBTITUTE AND PREPARATION PROCESS

BACKGROUND OF THE INVENTION

1. Field of the Invention

This invention relates to a process for the preparation of sucrose fatty acid polyesters and the resultant products; and more specifically, to the use of partially etherified sucrose as feedstock in the process. The products are particularly useful as synthetic low calorie fat substitutes for replacing triglyceride fats in food compositions.

The consumption of large amounts of triglyceride fats has been linked to various health problems. For example, one of the most common metabolic problems among people today is obesity. This condition is primarily due to ingestion of a greater number of calories than are expended. Fat is the most concentrated form of energy in the diet, with each gram of fat supplying approximately nine calories, and triglyceride fats constitute about 90% of the total fat consumed in the average diet.

In a U.S. government study, it has been reported that elevation of blood cholesterol levels is a major cause of coronary artery disease, and recommended a reduction in the amount of fat eaten to reduce blood serum cholesterol levels. Thus, there is a need for ways to reduce the amount of triglyceride fats in the diet, in order to reduce the health risks associated with these fats.

2. Discussion of Related Art

Sucrose fatty acid esters are conventionally prepared by transesterifying a lower alkyl ester of higher fatty acids with sucrose. Since sucrose has eight hydroxyl groups per molecule, the number of fatty acid groups bound to sucrose per molecule, commonly referred to as the degree of substitution (D.S.), may vary from 1 to 8. Among them, mono-, di-, and tri-esters find use as non-toxic, biodegradable surfactants and are commercially available in large quantities.

The various known methods for producing sucrose fatty acid esters may be classified into three principal types; i.e., the solvent process, the microemulsion process, and the direct or solvent-free process.

In the solvent process, a fatty acid ester is transesterified with sucrose in a common solvent for the fatty acid ester and sucrose such as dimethylformamide or dimethylsulfoxide in the presence of a basic transesterification catalyst. The reaction may be carried out at a relatively lower temperature, for example, at about 90° C. This process suffers from certain disadvantages in that the solvent used is toxic and, therefore, must be completely removed after the reaction. This is possible in practice only with great difficulty.

In the second process generally known as "microemulsion process", a fatty acid ester is dispersed in a solution of sucrose in a solvent such as propylene glycol or water with the aid of an emulsifier such as alkali metal fatty acid soaps to form a microemulsion, and then the solvent is removed from the emulsion. The reaction is carried out in the absence of solvent and the reaction product does not contain any solvent. Great difficulty is also present in this process for removing the solvent while maintaining the microemulsion state.

In the third process, sucrose is directly reacted with a fatty acid ester by heating their mixture. This process is known as "direct process" or "solvent-free process". Since sucrose and fatty acid esters do not have sufficient affinity to each other, the success of this direct process depends on how well they are contacted in the reaction system. To this end, most of known processes employ an alkali metal fatty acid soap either directly added to or formed in situ in the reaction system to produce a homogeneous molten mixture of reactants.

Consequently, the reaction mixture from the microemulsion process or direct process contains a relatively large amount of alkali metal fatty acid soap, since the soap itself is not a reactant and remains unreacted during the transesterification reaction.

A relatively small amount of alkali metal fatty acid soap is unavoidably formed even in the solvent process by the reaction between the fatty acid ester and the transesterification catalyst such as alkali metal hydroxides and carbonates.

Normally, alkali metal fatty acid soaps remaining in the reaction mixture are separated from sucrose fatty acid esters, while their presence may be tolerated in certain uses such as detergents.

Sucrose fatty acid polyesters may be produced by the following published microemulsion process or solvent-free process.

U.S. Pat. No. 3,963,699 to Rizzi et al. discloses a process for producing sucrose fatty acid polyesters. According to this process, a mixture of sucrose, a fatty acid lower alkyl ester, an alkali metal fatty acid soap and a basic catalyst is heated in the first step to form a homogeneous melt. Thereafter, excess fatty acid lower alkyl esters are added in the second step to the reaction product of the first step. This process suffers from certain disadvantages in that it requires basic transesterification catalysts such as alkali metals, alloys of alkali metals, alkali metal hydrides or alkali metal alkoxides which are expensive and dangerous in handling. The two step reaction is cumbersome in operation and necessarily requires a prolonged reaction time which can lead to the risk of darkening of the reaction mixture.

Generally, sucrose fatty acid esters having a D.S. of greater than 2 are produced by controlling the molar ratio of fatty acid lower alkyl esters to sucrose. Up to a D.S. of 5, polyesters may be prepared at the ratio of fatty acid esters approximately equal to or slightly in excess of theoretical amounts. However, polyesters having a D.S. of greater than 5 require further amounts of fatty acid lower alkyl esters. For example, polyesters having a D.S. of 5.5, 6 and 7 or higher may only be produced at the ratio of fatty acid esters of 6, 8 and 10 moles per mole of sucrose, respectively.

Thus, it is critical for the industrial production of sucrose fatty acid polyesters to minimize the amount of fatty acid lower alkyl esters. The presence of large amounts of fatty acid lower alkyl esters in the reaction system at one time produces certain unique problems. A reaction system containing a large amount of fatty acid esters is less viscous and thus easily susceptible to phase separation which adversely affects the transesterification reaction. Furthermore, relatively large amounts of low boiling point by-products such as methanol are generated and vigorous foaming of reactants takes place during the initial period of the reaction.

Fatty acid lower alkyl esters may be removed from the reaction product by solvent extraction using a solvent such as methanol in which sucrose fatty acid esters are relatively insoluble and fatty acid lower alkyl esters are soluble. However, this technique requires a large amount of solvent. For example, about 40 times of methanol are used relative to the sucrose fatty acid ester in the previously cited Rizzi et al. Patent. This is, of course, uneconomical and requires a large amount of investment for the solvent recovery system and anti-explosion facilities. Additionally, certain amounts of sucrose fatty acid esters dissolving in the solvent are unavoidably wasted.

Sucrose fatty acid polyesters are known as suitable low-calorie fat replacers in edible products. Substantially indigestible by human beings, they have physical and organoleptic properties very similar to triglyceride oils and fats conventionally used in edible products as described, for example, in U.S. Pat. Nos. 3,600,186, 4,005,195 and 4,034,083. In addition, U.S. Pat. No. 5,077,073 discloses ethoxylated sugar or sugar alcohol sucrose fatty acid esters useful as fat substitutes wherein from 1 to 50 alkoxyl groups are attached by ether linkages to each polyol molecule. However, the use of sucrose fatty acid polyesters which are liquid below body temperature (about 37° C.) has been reported to result in an undesired laxative effect and give rise to the problem of anal leakage. Thus to overcome this problem, it has been proposed to introduce considerable amounts of solids in the sucrose polyester phase by adding solid fatty acids, or employing a polyester which is partially liquid and partially solid at body temperature.

It is accordingly a main object of this invention to provide a process for producing sucrose fatty acid polyesters in an efficient manner which is free from the above-described disadvantages and which is simple in operation and easy to control.

DESCRIPTION OF THE INVENTION

Other than in the operating examples, or where otherwise indicated, all numbers expressing quantities of ingredients or reaction conditions used herein are to be understood as modified in all instances by the term "about".

It has now been found that sucrose fatty acid polyesters may be produced via a transesterification reaction by utilizing partially etherified sucrose as feedstock in combination with a fatty acid lower alkyl ester to prepare sucrose polyesters useful as synthetic low calorie fat substitutes in foods. Sucrose ethers are mixtures of mono- to octa-octyl ethers of sucrose. The sucrose ethers may be obtained by the telomerization reaction of butadiene with sucrose to give the respective octadienyl ethers, and subsequent hydrogenation to the saturated product, wherein the average degree of substitution or etherification (average number of octyl groups/sucrose) can be varied by changing the ratio of butadiene and sucrose during the reaction. The use as a reactant of partially etherified sucrose having a minimum degree of substitution enables sufficient oil solubility to allow for facile reaction with fatty acids, fatty acid esters or triglycerides to produce the desired sucrose polyester.

In accordance with this invention, sucrose fatty acid polyesters are prepared from sucrose ethers having an average degree of etherification of about 4, i.e., about 50% of the hydroxyl groups are etherified, although the degree of etherification may range from 1 to 8, it is preferably 3 to 6.

Thus, in a broad sense, the process of this invention comprises mixing a sucrose ether having an average degree of etherification of about 3 to 6, preferably about 4, with a basic catalyst and an excess of a fatty acid lower alkyl ester, heating the mixture to a temperature of from about 120° C. to about 180° C. at a pressure of up to about 10 mm of mercury while removing the alcohol formed during the formation of the sucrose fatty acid polyesters, and then separating the sucrose fatty acid polyesters from the reaction mixture. Separation can be accomplished by any of the separation procedures routinely used in the art. Distillation, water washing, conventional refining techniques or solvent extraction are preferred due to their simplicity and economy. The product may also be bleached, if desired, with a bleaching agent. The sucrose ethers may be esterified to a degree of close to 100%.

The term "sucrose fatty acid polyesters" as used herein refers to these having an average degree of substitution of about 4 to about 8.

Esters of lower alcohols, preferably $C_{1-4}$ alcohols, are suitable for use as fatty acid lower alkyl esters. The term "fatty acid lower alkyl esters" as used herein is intended to include the $C_1$ to $C_4$ alkyl esters of fatty acids containing 6 to 22 carbon atoms., The fatty acids may be saturated or unsaturated and may have a straight or branched chain. Mixtures of fatty acid esters may also be used. From 4 to 15 moles, preferably from 8 to 15 moles of fatty acid lower alkyl esters per mole of sucrose ether are used. Methyl esters are the preferred fatty acid esters for use herein, since their use in the process tends to result in unusually high yields of sucrose fatty acid polyesters.

Examples of suitable fatty acids containing 6 to 22 carbon atoms include caprylic, capric, lauric, myristic, myristoleic, palmitic, palmitoleic, stearic, oleic, ricinoleic, linoleic, linolenic, eleostearic, arachidic, arachidonic, behenic and erucic acid. The fatty acids can be derived from naturally occurring or synthetic fatty acids, they can be saturated or unsaturated, including positional and geometrical isomers. The fatty acids esterified to the sucrose ether molecule are preferably of mixed carbon chain length to produce the desired physical properties.

In a preferred embodiment of this invention, the fatty acid residues of the non-digestible sucrose polyesters contain less than about 10 wt. % fatty acid residues having a carbon chain length of 10 or less. It has furthermore been found beneficial to include a significant amount of fatty acid residues having a carbon chain length of 13 to 17, and to select the majority of fatty acid residues from those having a carbon chain length of 14 to 18 carbon atoms. Accordingly, it is preferred that at least 50 wt. % of the fatty acid residues of the non-digestible sucrose fatty acid polyesters have a carbon chain length of 13–17, and more preferably more than 50 wt. % of the fatty acid residues have a carbon chain length in the range of 14–18. In addition, it is also preferred that less than 10 wt %, more preferably less than 5 wt % of the fatty acid residues in the non-digestible sucrose fatty acid polyesters of this invention have a carbon chain length of 20 or more.

The physical properties of sucrose polyesters, like those of triglyceride fats, depend on the fatty acids used in preparation of the material. The fatty acids esterified to the sucrose ether dictate the physical properties of the resulting fat substitute ranging from a liquid to a solid. For example, sucrose polyester made from safflower oil fatty acids ($C_{18}$) is a free-flowing liquid similar to safflower oil. By comparison, sucrose polyester made from a completely saturated long-chain fat, e.g. lard, is a high-melting solid at room temperature. Generally, sucrose fatty acid polyesters are virtually identical in physical properties to a triglyceride with the same fatty acids. Taste, appearance, aroma and immiscibility with water are indistinguishable from triglyceride. It is these properties, along with their non-absorption, i.e., resistance to pancreatic lipase activity, which give sucrose fatty acid polyesters their unique qualities and value as non-calorie fats or oils for use in foods. Thus, sucrose polyesters provide the perception of fat to foods without delivering the calories normally assimilated when triglycerides are consumed.

In the preparation process of the sucrose fatty acid polyesters of this invention, examples of basic transesterification catalysts include alkali metal carbonates such as potassium carbonate and sodium carbonate, alkali metal hydroxides such as potassium hydroxide and sodium hydroxide, and alkali metal lower alkoxides such as potassium methoxide and sodium ethoxide, and alkali metal hydrides. Sodium hydride is a preferred catalyst because better results have been obtained therewith in the process of this invention. The catalyst is added to the reaction mixture in an amount of from about 0.10 to about 0.20%, preferably about 0.15% by weight of fatty acid lower alkyl ester. The fatty acid lower alkyl ester serves also as a carrier or dispersing agent for the catalyst to insure uniform distribution of the catalyst throughout the reaction mass. Methanol may also serve as a carrier or dispersing agent for the catalyst.

The transesterification reaction may be carried out by heating the reaction mixture at a temperature of 120° C. to 180° C., preferably from 140° C. to 160° C., under a vacuum less than 10 mm Hg with stirring at a linear speed of 1 to 50 m/second, preferably from 2 to 20 m/second.

The length of reaction time varies with the reaction conditions and ,generally requires only 1 to 3 hours.

As previously noted, as the transesterification reaction proceeds, a lower alcohol is formed as a by-product. In order to promote the reaction, the alcohol by-product is preferably removed. Many removal techniques are known in the art, and any one of them can be used to effectively and efficiently remove the lower alcohol. Vacuum removal both with and without an inert gas sparging has been found to promote the reaction. In any event, the formation of a lower alcohol presents no significant obstacle to the use of the process in the food industry.

As used herein, the term "non-digestible" means being absorbable to an extent of 70% or less, and particularly 20% or less, by the human body through its digestive system.

The edible composition according to the present invention may contain in addition to the sucrose fatty acid polyesters minor ingredients conventionally found in frying oils including anti-foams, such as silicon oils, anti-spattering agents, anti-oxidants, such as naturally present or added tocopherols, butylated hydroxytoluene, -anisole or -quinone, acids such as citric acid, ascorbic acid, flavouring agents, and the like.

The sucrose fatty acid polyesters of this invention may be present in compositions such as frying fats, cooking oils, shortenings, margarines, spreads, ice cream, dressings, and the like. The sucrose polyesters are particularly suitable for shallow and deep frying purposes. Thus, another aspect of this invention is the use of the instant sucrose fatty acid polyesters for preparing fat-containing edible food products wherein the process involves heat treating at least part of such food products with a fluid fat comprising said polyester composition at a temperature of more than about 100° C. When using the present composition in, for instance, deep frying or shallow frying food products, the products will not rapidly develop a solid fat layer after having been taken out of the hot oil. In some cases, it may be advantageous to combine the sucrose polyesters of this invention with relatively low melting glyceride fats having a melting temperature below body temperature because such combinations provide products that exhibit no drip-off problems and have very good frying properties. In such case, the frying fat composition may comprise from 70% to 90% by weight of the sucrose fatty acid polyesters and from 10% to 30% by weight of glyceride fats. Suitable glyceride oils and fats include those optionally modified by partial hydrogenation and/or fractionation to provide the required melting characteristic, such as coconut oil, palmkernel oil, palm oil, butter fat, soybean oil, safflower oil, cotton seed oil, rapeseed oil, poppy seed oil, corn oil, sunflower oil, tallow, lard and mixtures thereof. Of these oils, palm oil, partially hardened rapeseed oil and partially hydrogenated soybean oil are preferred. Accordingly, another aspect of this invention is edible fried food products that have been fried in a frying fat or oil composition pursuant to the invention. Food products which can suitably be fried in the present frying fat composition include: potato crisps (french fries), potato and corn chips, fried snacks, fried chicken, meat and fish products, battered and crumbed fish and meat products such as e.g. fish sticks and the like. At the point of sale these food products may either be fully baked, or be in a frozen pre-fried condition requiring further preparation by oven or microwave.

The invention is further illustrated by the following example, but it is not intended to be limited thereby.

The following reaction was carried out in a 1 liter 3-neck flask containing a stirrer, thermometer, reflux condenser, and vacuum outlet.

EXAMPLE

A sucrose ether having an average degree of etherification of about 4, and about 50% excess of a methyl oleate esterifying agent were degassed, and about 0.16%/wt. of a sodium hydride catalyst was added thereto. After evolution of hydrogen gas had stopped, the mixture was heated to a temperature of about 85° C. under a nitrogen blanket for about 1½ hours. After most of the methanol had distilled off, high vacuum at about 135° C. was applied for about 2 hours to remove the remaining methanol. The product was cooled to about 25° C. and extracted with methyl alcohol to remove excess methyl oleate. The product having a light brown color, was bleached to a light yellow color using grade 160 filtrol (clay).

The following examples illustrate lipase enzyme assay used as a screening test for animal feeding studies.

A stabilized test oil emulsion is incubated overnight with lipase and buffer of pH 8.0. The test oil is hydrolyzed by pancreatic lipase to fatty acids, diglycerides and to a small extent monoglycerides and glycerol. The fatty acids liberated in the reaction are titrated with 0.050N NaOH to a pH of 10.5.

In a 15×45 mm, 4 ml vial are combined the following: 0.5 ml $H_2O$; 0.5 ml of 7 percent(w/v) gum acacia (gum arabic); 0.5 ml of candidate oil and 0.2 ml of 0.2M tris buffer pH 8.0 (tris(hydroxymethyl) aminomethane which is available from Sigma Chemical Co., St. Louis, Mo.). To save time and steps, in practice, the water, gum acacia, and buffer are combined into a stock solution (10–20 ml) and an aliquot of 1.2 ml of this mixture is added to 500 microliters of test oil in the vial. Each test run will contain a sample of olive oil emulsion prepared in the same way which serves as a positive control to determine the activity of the lipase and the effectiveness of the emulsification.

The contents of each vial are then sonicated for no more than 10 cycles (power=4; duty=50 percent) in a Tekmar sonic disrupter (Tekmar Company, Cincinnati, Ohio) equipped with a standard microtip probe. The probe is wiped between samples with a Kimwipe moistened with EtOH or $CHCl_3$.

The result is a stable, creamy white emulsion. Eight each 135 microliter samples are distributed to 21×70 mm. 16 ml sc vials. The four test vials receive 10 uL each of a cocktail containing 10 percent w/v of each of the following lipases in deionized water: lipase N, lipase G and lipase D (available from Amano International Enzyme Co., Inc., P.O. Box 1000, Troy, Va. 22974). The blanks receive no enzyme at this stage. All of the vials are capped and incubated overnight at 37° C. The unused lipase stock is also capped and incubated overnight at 37° C. This permits any enzymatic reactions which might alter pH to take place.

For each day's titration, a fresh one liter batch of 0.05 N NaOH is prepared by diluting 1:10 a 100 ml sample of purchased 0.5N NaOH reagent. The 0.05N NaOH is also standardized against a 0.1N HCl sample by titration to pH 7.0. All of these steps ensure the accuracy of the titration data.

For each sample of oil, the eight tubes are removed from the 37° C. incubator. Each tube receives the addition of a ⅜ inch diameter TFE starburst stirring head (available from Fisher Scientific Co.) magnetic stirrer and 4.0 ml of $H_2O$ to increase the volume and allow the pH electrode to be submerged. The four "blank" tubes receive 10 microliters of the overnight incubated lipase stock solution immediately prior to titration.

All samples are then titrated to pH 10.5 in a Fisher Computer Aided Titrimeter equipped with a Gel-Filled Polymer Body Combination pH electrode (available from Fisher Scientific Co.). The average number of mls added to the blank sample are subtracted from the average number of ml added to the test sample to determine the mL OH required to neutralize the acid from 50 microliters of oil.

From the determined value of density for the oil, a value of lipase liberated milliequivalents of acid per gram of oil is computed. This value is divided by the value for total available acid determined by saponification of a measured mass of test oil. From this ratio, a value for percent lipase hydrolysis is computed. The results are summarized in Table 1.

TABLE 1

Lipase Hydrolysis Test Results

| Sample | % Lipase Hydrolysis | |
| --- | --- | --- |
| | (1 hour) | (18 hours) |
| Sucrose ether methyl oleate polyester | 1–2 | 1–2 |
| Control-olive oil | 53–55 | 73–75 |

The above-identified sucrose polyester was tested for its minimal absorption potential as a non-nutritive substance. The criteria for a non-nutritive oil are that a successful candidate will be safe for human consumption, be less than 40% absorbed, not cause anal leakage at projected exposures, and exhibit thermal stability for use in fried foods. These beneficial qualities in a food oil will provide the consumer with a new product that has the potential to lower fat intake and thereby lower the high caloric consumption perceived with fried foods, e.g. snack foods.

Test Materials and Methods

An intact biological system (live animal) is required to study the interaction of digestion, absorption, and metabolism by various organs. Fischer 344 rats were chosen as the animal model due to the extensive, historical toxicological experience with this rat strain. After arrival, the animals were held for one week to acclimate to the change in living environment, and one week for diet habituation prior to the actual test phase. Three dose levels, 2.5%, 5.0%, and 7.5%, of the test compound were evaluated for a two-week study period. Body weight gain and food consumption were monitored throughout the two-week test period. Feces were collected from the low-dose groups during the second study week for determination of oil absorption using Soxhlet oil analysis. Upon termination, a gross necropsy was performed to reveal any evidence of gross pathological changes that occurred while the test compound was fed. Samples of blood serum were taken for hematology and clinical chemistry analysis. The blood serum and livers were analyzed by TLC for the presence of test oil. This study was intended as a discovery screening vehicle and was not conducted according to GLP guidelines. The study was conducted in all aspects with sound scientific practices.

Results and Discussion

The absorption data were corrected for the actual quantity of oil in the diet. Spiking of control fecal samples revealed that all test oils were adequately recovered (average of greater than 92% recovery) by Soxhlet oil analysis.

The sucrose polyester met the criteria for less than 40% absorption. No deaths occurred during the two-week testing period. No evidence of gross toxicity was observed with the test oil. Unusual vasodilation was observed in association with the reproductive organs of both sexes. Females from two dose groups were observed to have unusually vascularized ovarian follicles, or a blood engorged (hematoma) ovary. Further studies would necessitate an indepth histological and pathological evaluation of this phenomena, to determine its biological significance. However, it is known that certain of the impurities (especially fatty acid methyl esters) may exhibit activity on smooth muscles, particularly vascular smooth muscle, and thus these results may be secondary to the presence of impurities.

Animals in all test groups (including control animals) exhibited lymphoid Peyer's patch hyperplasia, a nonspecific immune response. Although the antigenic agent causing this response is unknown, this common finding should not affect the data interpretation.

Liver to body weight ratios were lower than controls for the high dose male groups. Higher liver to body weight ratios than controls were observed in the medium dose group. These findings (which are virtually opposite and thus not dose-response related) are not coupled with significant changes in the liver enzyme activities associated with toxicity, and are therefore probably of little biological significance.

No differences were observed in spleen weights or spleen to body weight ratios. Body weights and weight gain were monitored throughout the study. No differences were observed between termination body weights (within the same sex groups). No differences were observed between the rates of growth (within the same sex groups).

Fecal weights were found to be higher in males with poorly absorbed sucrose polyester. Anal leakage was present in the high dose group of the test compound. Nonabsorption of the test oil appeared to be not the only contributing factor to anal leakage in this study. Other undetermined factors also appear to have played a key role.

Food consumption was monitored during the study, and the data were used to calculate feed efficiency. More food was consumed by the animals in the high dose sucrose polyester group than the controls. Evaluation revealed a reduction in feed efficiency for the high dose male group. This is probably a reflection of the severe anal leakage observed in this group.

A few statistically significant differences were observed with clinical chemistry values analysis. One significant effect observed with males fed the sucrose polyester was a reduction in total protein levels. This reflects a drop in the quantity of proteins circulating in the blood serum. Serum albumin is the major protein constituent of blood serum; however, its titer was unchanged. Therefore, the changes in blood protein are probably due to other components, possibly acid glycoprotein or immune system constituents. The magnitude of the change, however, is small (about 6%) and no comparable change was found in females. Thus, the biological significance of this change is unknown.

No test compound was detected by TLC analysis of extracts made from blood serum and liver with a detection limit of 0.5% (v/v). This implies that any absorbed test material was extensively metabolized.

What is claimed is:

1. The process of preparing a sucrose fatty acid polyester comprising mixing a sucrose ether having an average degree of etherification of from about 3 to about 8 with a basic catalyst and an excess of a fatty acid lower alkyl ester, heating the resultant mixture to a temperature of from about 120° C. to about 180° C. at a pressure of up to about 10 mm of mercury while removing the alcohol formed during the formation of said sucrose fatty acid polyester, and then separating said sucrose fatty acid polyester from the reaction mixture.

2. A process as in claim 1 wherein said sucrose ether has an average degree of etherification of from about 3 to about 6.

3. A process as in claim 1 wherein said lower alkyl ester comprises a $C_1$–$C_4$ alkyl ester of a fatty acid containing 6 to 22 carbon atoms.

4. A process as in claim 1 wherein said lower alkyl ester comprises a fatty acid methyl ester.

5. A process as in claim 4 wherein said methyl ester is derived from a fatty acid selected from the group consisting of saturated fatty acids, unsaturated fatty acids, and mixtures thereof.

6. A process as in claim 1 wherein from about 4 to about 15 moles of said fatty acid lower alkyl ester is used per mole of said sucrose ether.

7. A process as in claim 1 wherein said catalyst is selected from the group consisting of an alkali metal carbonate, alkali metal hydroxide, alkali metal lower alkoxide, and alkali metal hydride.

8. A process as in claim 1 wherein said catalyst is present in said mixture in an amount of from about 0.10 to about 0.20 percent by weight, based on the weight of said fatty acid lower alkyl ester.

9. A process as in claim 1 including bleaching said sucrose fatty acid polyester.

* * * * *